United States Patent [19]

Todd

[11] 4,420,722
[45] Dec. 13, 1983

[54] TESTING SEMICONDUCTOR FURNACES FOR HEAVY METAL CONTAMINATION

[75] Inventor: Albert A. Todd, Mountaintop, Pa.

[73] Assignee: RCA Corporation, New York, N.Y.

[21] Appl. No.: 206,715

[22] Filed: Nov. 14, 1980

[51] Int. Cl.³ .................... G01N 27/00; G01N 27/12; G01N 31/22

[52] U.S. Cl. .................... 324/158 R; 73/23; 324/71.5; 357/89; 422/98

[58] Field of Search .......... 324/158 R, 158 D, 158 T, 324/71 SN, 65 R, 71.5; 357/89; 73/23; 422/98; 436/151

[56] References Cited

U.S. PATENT DOCUMENTS

| | | |
|---|---|---|
| 2,827,436 | 3/1958 | Bemski . |
| 2,965,842 | 12/1960 | Jacobson . |
| 3,865,550 | 2/1975 | Bott et al. .......................... 307/304 |
| 3,879,985 | 4/1975 | Maslen .............................. 324/65 R |
| 4,135,951 | 1/1979 | Stone ..................................... 357/91 |
| 4,216,038 | 8/1980 | Nishizawa et al. ................... 357/89 |
| 4,239,558 | 12/1980 | Morishita et al. ..................... 357/89 |
| 4,283,236 | 8/1981 | Sirsi ..................................... 357/89 |

Primary Examiner—Ernest F. Karlsen
Attorney, Agent, or Firm—Birgit E. Morris; Donald S. Cohen; Robert P. Seitter

[57] ABSTRACT

A technique for testing for heavy metal contamination in semiconductor processing furnaces includes use of a chip having a plurality of PN- junctions, at least one of which is completely isolated from the sides of the chip. The chip is manufactured to exhibit a high reverse recovery time and this can be conveniently accomplished by a combination of a gettering layer to getter the heavy metal atoms away from the junction and by never raising the temperature of the chip above 800° C. after the gettering layer is provided.

In use, the chip is fed through a furnace either with or, preferably before the wafers being processed, which is operating at the conditions under which semiconductor devices are to be processed. After the chip is removed from the furnace, its reverse recovery time is measured and compared to its initial reverse recovery time to determine if it has decreased.

5 Claims, 5 Drawing Figures

TESTING SEMICONDUCTOR FURNACES FOR HEAVY METAL CONTAMINATION

BACKGROUND OF THE INVENTION

This invention relates to the detection of heavy metal contaminants in a furnace in which semiconductor devices are to be processed. During their manufacture, semiconductor devices are repeatedly heated to elevated temperatures. The presence of heavy metal contaminants, for example, nickel, iron, gold or copper, in any one of the heating furnaces introduces heavy metal atoms into the semiconductor device being processed and these atoms cause an ofttimes undesirable decrease in minority carrier lifetime and an increase in leakage current of a reverse biased junction.

As part of the quality control function in semiconductor manufacturing operations, the heavy metal contamination in a furance is monitored so that corrective action can be taken if the furnace is contaminated. One such monitoring technique is to measure the reverse recovery time of the devices being processed after the wafer is removed from a furnace. If the reverse recovery time is lower than expected for the type of device being processed, it would indicate the presence of heavy metal contaminants. With this technique, however, monitoring can not begin until the PN junctions are formed. Thus, this technique is after the fact and needless expense may have been incurred in processing numerous wafers. Finally, since the devices being processed vary significantly, a data base of expected reverse recovery time for each device being processed must be maintained. Accordingly, the above technique is not entirely satisfactory.

Another technique for monitoring contamination is a surface photovoltage technique in which light is directed on the surface of the wafer to determine how much light is absorbed. The more light absorbed, the more heavy metal contaminants are present. This technique is not sufficiently sensitive to detect low contamination levels in the device. Another technique has been to measure the capacitance versus voltage of the device. This technique works for the detection of sodium contamination, but has not shown any reliable correlation with heavy metal contamination.

SUMMARY OF THE INVENTION

In accordance with this invention there is provided a test device for use in a testing process to monitor heavy metal contamination in a semiconductor furnace. The test device comprises a chip of semiconductor material having a pair of major surfaces. The chip further comprises a first outer region heavily doped with impurity atoms of one conductivity type extending into the chip from one major surface and an intermediate region doped with a lesser concentration of impurity atoms of the same type. From the other major surface of the chip there extends a plurality of outer regions doped with impurity atoms of the opposite conductivity type that define with the intermediate region a plurality of PN junctions. At least one of the second outer regions is completely surrounded by an isolating region.

In making the device, there is provided a high resistivity wafer of the one conductivity type. A heavier concentration of impurity atom of that conductivity type are diffused into the one major surface and also into the isolation regions on the other major surface. Thereafter, impurity atoms of the other conductivity type are diffused in the regions between the isolation regions to provide the plurality of PN junctions. Finally, the wafer is broken into chips such that each chip includes a plurality of PN junctions, at least one of which is completely isolated. After the atoms of the one conductivity type are diffused into the wafer, the wafer is never subjected to a temperature in excess of 800° C. during the remainder of the manufacturing process.

In order to monitor the furnace atmosphere, the chip is conveyed through the furnace operating under conditions at which the semiconductor device is to be processed. After the chip is removed from the furnace, the reverse recovery time is measured through the isolated PN junction and the measured reverse recovery time is compared to the reverse recovery time before the furnacing to see if the reverse recovery time has decreased. Such a decrease indicates the presence of heavy metal contaminants in the furnace.

BRIEF DESCRIPTION OF THE DRAWING

For a better understanding of the invention, reference is made to the following description of a preferred embodiment thereof, taken in conjunction with the figures of the accompanying drawing, in which.

DETAILED DESCRIPTION OF A PREFERRED EMBODIMENT

Figure 5:
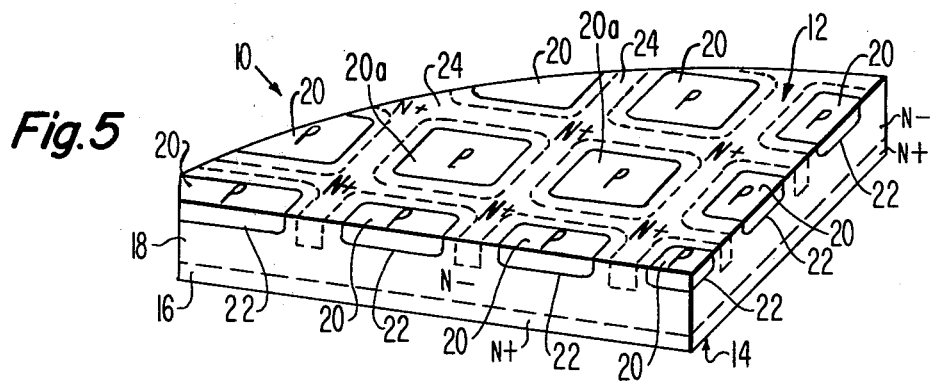
FIG. 5 is a perspective view of a test chip in accordance with this invention.

Referring first to FIG. 5, there is illustrated a chip 10 of semiconductor material having a pair of major outer surfaces 12 and 14 which is particularly useful for monitoring heavy metal contamination in a furnace in which semiconductor devices are to be processed. For accomplishing this function, the chip 10 is constructed and arranged to have a relatively high reverse recovery time. Accordingly, the chip 10 includes a first outer N+ region 16, that is a region heavily doped with impurity atoms of the N conductivity type. This region 16 extends inwardly from major surface 14 a relatively short distance so that it is relatively thin. Adjacent the outer region 16 is an intermediate N— region 18 that is a region very lightly doped with impurity atoms of the N conductivity type.

Figure 4:
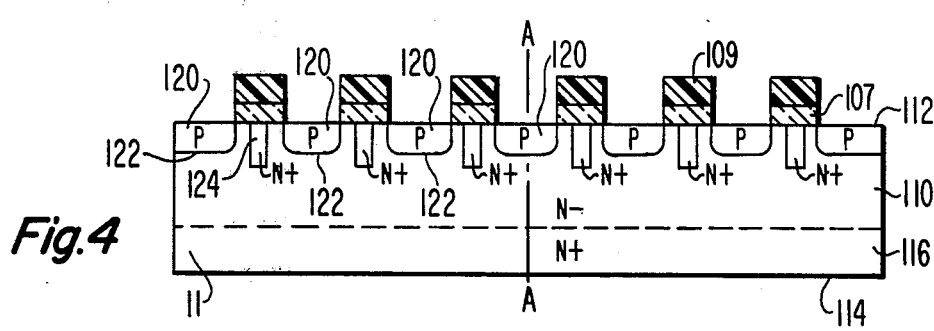

Extending inwardly from the major surface 12 are a plurality of P regions 20, that is, regions doped with normal concentrations of impurity atoms of the P conductivity type. Thus, there are formed a plurality of PN— junctions 22 located closely adjacent the surface 12. Isolation regions are located between the P type regions 20 to electrically isolate these regions from each other. In the preferred embodiment disclosed herein, the isolation means comprises N+ channels 24, that is, channel shaped regions highly doped with impurity atoms of the N conductivity type. The isolation channels 24 extend to a depth at least equal to and preferably slightly deeper than the P type regions 20 so that they are closer to the major surface 14 than the junctions 22. The isolation regions 24 extend parallel and perpendicular to each other as illustrated in FIG. 4. Some of the P type regions 20 adjacent the sides of the chip 10 may not be confined by the isolation means 24, but each chip includes at least one P type region that is completely isolated, that is, bordered on all sides by the isolation means so that it is completely isolated from the sides of the chip and not susceptible to surface effects and its resultant variations in the characteristics of the device. In the preferred embodiment illustrated in FIG. 5, two such isolated regions are illustrated and are denoted by reference numerals 20a.

In the preferred embodiment illustrated here, the N+ isolation channels 24 are slightly spaced from the P regions 20 by more lightly doped N type material so that the actual vertical junction between regions 20 and the channels are PN− junctions. It should be understood, however, that the N+ isolation channels 24 could extend to the P type regions 20 providing vertical PN+ junctions. Use of the PN− junctions is preferred in order to maximize the reverse recovery current through the device.

In use, the control chip 10 is conveyed through a furnace in which semiconductor devices are to be processed. During this time the furnace is operating at the conditions under which it will operate when processing the semiconductor devices. Usually the temperature in the furnace will be greater than 800° C. Since the chips are standard, their reverse recovery time is known before the conveyance and for all such chips, it should be approximately equal. After the chip 10 is removed from the furnace, its reverse recovery time is measured. Such measurement is generally done in accordance with standard techniques which includes the application of a forward bias for a period of time and then a reverse bias during which the reverse recovery time is measured. In order to minimize the surface effects, the forward and reverse bias is applied across one of the completely isolated PN− junctions. That is, one terminal is placed across the N+ outer region 16 and the other terminal is applied to one of the isolated P type regions 20a. If the reverse recovery time after furnacing is equal to or, in some cases, only slightly less than the reverse recovery time before furnacing, the chip 10 has not been contaminated with heavy metal atoms, it being understood that heavy metal contamination decreases reverse recovery time. If, on the other hand, the reverse recovery time has decreased, it indicates that heavy metal atoms are present and these heavy metal atoms have been diffused into the test device 10 in the furnace. Thus, corrective action can be taken to lower heavy metal contamination in the furnace. The test chip 10, can be conveyed through the furnace with semiconductor devices as they are processed, but preferably, are conveyed through the furnace before any such devices are processed. In this way, if the furnace is contaminated with heavy metal, the needless expense of processing wafers has been avoided.

The chip 10 is well suited for such testing. It is constructed so that its reverse recovery time, before furnacing, is relatively high so that an easily discernible difference is provided if the furnace is contaminated with heavy metal. In addition, the chip 10, including a plurality of PN junctions, is relatively large so that it is easy to handle and is not so fragile as to be easily broken. By completely isolating one of the PN− junctions and by making the measurement across such a junction, the reliability of the measurement is assured because surface effect variations are eliminated. The use of a PN− junction in itself provides for the relatively high reverse recovery time and the use of the N+ outer region 14 getters heavy metal atoms in the furnace in which the chip 10 is itself made.

Figure 1:
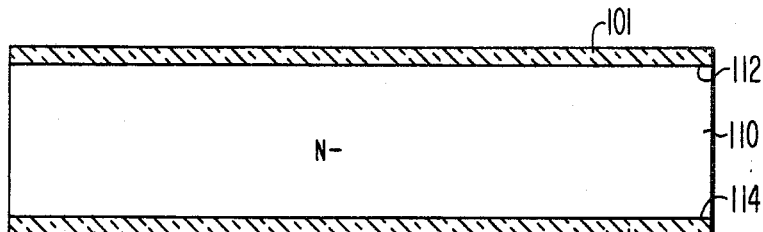
FIGS. 1-4 illustrate a method of making a test chip in accordance with this invention.

Finally, the chip 10 is manufactured under conditions that assure it has a relatively high reverse recovery time. A preferred technique for manufacturing the chip 10 will now be disclosed. Referring to FIG. 1 of the drawing, the starting material for the test chip 10 is a silicon wafer 110 having major surfaces 112 and 114. The wafer can be of a conventional size on the order of up to 9 or 10 mils thick and about 2 inches in diameter. The wafer 110 is light doped with N type atoms, preferably, phosphorus, in any conventional manner. For example, the phosphorus atoms may be introduced into the melt from which the silicon wafer is grown. The wafer is then cleaned in a conventional manner using a sulfuric peroxide cleaning solution. Thereafter, the wafer is placed in a furnace at an elevated temperature of 800° C. The introduction of the wafers into the furnace is relatively slow being on the order of about 3 inches per minute to minimize dislocations in the wafer which could minimize the lifetime of the minority carriers and therefore the reverse recovery time. After the wafers are in the furnace, the temperature is ramped up from 800° C. to 1100° C. at the rate of 3° C. per minute. Steam is introduced into the furnace where the chip remains for a period of about 5 hours to grow oxide ($SiO_2$) layers 101 and 103 on the major surfaces 112 and 114, respectively. Afterwards, the wafer is slow cooled from 1100° to 800°. This is also done at the rate of 3° C. per minute.

Figure 2:
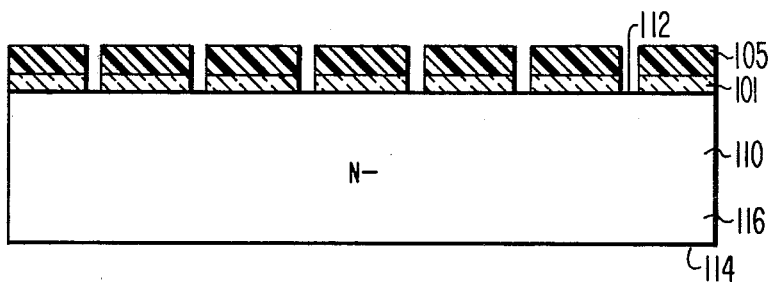

As seen in FIG. 2, a mask 105 is placed over the oxide layer 101 on the major surface 112. The mask 105 is a photoresist processed in accordance with generally conventional photolithographic techniques to leave unprotected those regions where the isolation regions 24 are to be formed. At this point, the $SiO_2$ layer 103 and portions of the layer 101 left unprotected by the mask are removed with a suitable etchant, for example, ammonium fluoride ($NH_4F$). The mask 105 is now stripped from the wafer.

Figure 3:
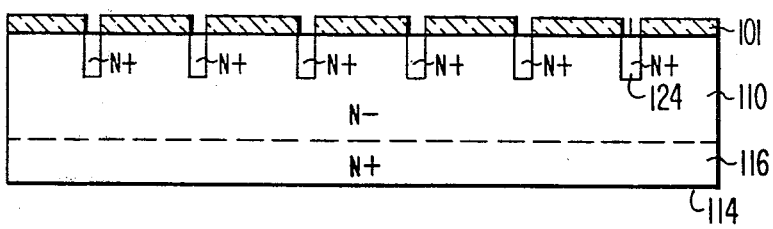

N+ type atoms are now deposited on and diffused into the exposed portions of the major surface 112 and the major surface 114. This can be accomplished in a suitable diffusion furnace containing an atmosphere of phosphorus oxychloride ($POCl_3$) heated to a temperature of about 1200° C. The wafer 110 is placed into the heated furnace with no phosphorus oxychloride for a period of about 10 minutes to heat the wafer. Thereafter, the phosphorus oxychloride is introduced into the furnace for an additional 10 minute period during which the phosphorus atoms are deposited on the unprotected surfaces of the wafer. After deposition, the flow of phosphorus oxychloride is discontinued and the chip is retained in the heated furnace for a period of about 30 minutes to diffuse the phosphorus atoms into the wafer. As shown in FIG. 3, such diffusion produces N+ channel regions 124 corresponding to the isolation regions 24 disclosed with respect to FIG. 5 and also to form an N+ region 114 corresponding to the region 14.

After the wafer is removed from the furnace, the oxide layer 101 is removed in any conventional manner, for example, by etching with hydrofluoric acid (HF) for a period of about 2 minutes. Now, additional oxide layers are grown on the surfaces 112 and 114 of the wafer in a manner similar to the layers 101 and 103. Only a portion of the oxide layer grown on surface 112 is shown in the drawing and is denoted by reference numeral 107. Another mask 109 is placed over the oxide layer 107 to leave unprotected those areas where the P regions 20 are to be formed. The mask 109 is a photoresist processed in accordance with conventional photolithographic techniques to define the protected and unprotected areas. After the mask 109 has been applied, the oxide is again etched from the surface 114 and the unprotected regions of the surface 112.

P type atoms are now deposited and diffused into the unprotected areas of the surface 112 as shown by reference numerals 120 to form the P type regions 20. It is important, here, to note that after the deposition and diffusion of phosphorus atoms to form the N+ regions in the wafer, the wafer is never again raised to a temperature above 800° C. during processing. Raising the wafer above that temperature increases its susceptibility to heavy metal atoms during that process and this could, in turn, reduce the reverse recovery time of the test chip. A suitable technique for depositing the P type atoms is to utilize ion implantation and diffusion techniques. With such techniques, boron ions are implanted into the unprotected regions of the surface 112. Preferably, a surface concentration of $2 \times 10^{15}$ is provided. After implantation, the wafer is placed in a nitrogen atmosphere at 800° C. for about 30 minutes. Exposure to this elevated temperature anneals the wafer to repair surface damage done to the unprotected regions of the surface 112 by the implantation and also diffuses the boron atoms inwardly into the unprotected N− regions to form relatively shallow PN− junctions 122 corresponding to junctions 22 previously explained with respect to FIG. 4.

After the wafer is removed from the furnace, it is scribed in accordance with generally conventional techniques and broken into pieces each of which includes a plurality of P regions 120 at least one of which is completely isolated. As shown in FIG. 4, the wafer 110 is broken into quarters along perpendicular diameters, one of which is illustrated by line A—A.

While in the foregoing there has been described a preferred embodiment of the invention, it should be obvious to those skilled in the art that various changes and modifications can be made without departing from the true spirit and scope of the invention as recited in the appended claims.

I claim:

1. A method of testing a semiconductor processing furnace for heavy metal contamination, said method comprising:

providing a chip of semiconductor material having first and second major surfaces, an outer N+ region extending into said chip from the first major surface, an intermediate N− region extending into said chip from the second major surface, a plurality of outer P regions extending into said chip from the second major surface so as to form a plurality of junctions with the N− intermediate region, and an N+ isolation region extending into said chip from the second major surface, said N+ isolation region being located between the P regions so as to electrically isolate the P regions from each other and from the side surface of the chip;

conveying said chip through the furnace to be tested while the furnace is operating under normal processing conditions;

measuring the reverse recovery time of said chip after it is withdrawn from said furnace; and determining if the reverse recovery time has decreased.

2. A method in accordance with claim 1 wherein the reverse recovery time is measured across said one of said junctions.

3. A test device for use in monitoring heavy metal contamination in a semiconductor processing furnace, said device comprising a chip of semiconductor material having first and second major surfaces, an outer N+ region extending into said chip from the first major surface, an intermediate N− region extending into said chip from the second major surface, a plurality of outer P regions extending into said chip from the second major surface so as to form a plurality of junctions with the N− intermediate region, and an N+ isolation region extending into said chip from the second major surface, said N+ isolation region being located between the P regions so as to electrically isolate the P regions from each other and from the side surface of the chip.

4. A test device in accordance with claim 3 wherein said outer N+ region and outer P regions are relatively thin and said intermediate region is relatively thick.

5. A test device in accordance with claim 3 wherein said N+ isolation region extends from said second major surface to a depth greater than that of said outer P regions.

* * * * *